(12) United States Patent
Viehland et al.

(10) Patent No.: US 11,589,746 B2
(45) Date of Patent: Feb. 28, 2023

(54) OPTICAL COHERENCE TOMOGRAPHY IMAGING SYSTEMS, HANDHELD PROBES, AND METHODS THAT USE A FIELD CURVATURE TO MATCH A CURVED SURFACE OF TISSUE

(71) Applicant: Duke Univesity, Durham, NC (US)

(72) Inventors: Christian Viehland, Durham, NC (US); Cynthia Toth, Durham, NC (US); Joseph Izatt, Durham, NC (US)

(73) Assignee: Duke University, Durham, NC (US)

( * ) Notice: Subject to any disclaimer, the term of this patent is extended or adjusted under 35 U.S.C. 154(b) by 323 days.

(21) Appl. No.: 16/955,138

(22) PCT Filed: Jan. 24, 2019

(86) PCT No.: PCT/US2019/015036
§ 371 (c)(1),
(2) Date: Jun. 18, 2020

(87) PCT Pub. No.: WO2019/147871
PCT Pub. Date: Aug. 1, 2019

(65) Prior Publication Data
US 2020/0315447 A1 Oct. 8, 2020

Related U.S. Application Data

(60) Provisional application No. 62/621,078, filed on Jan. 24, 2018.

(51) Int. Cl.
*A61B 3/10* (2006.01)
*A61B 3/12* (2006.01)
(Continued)

(52) U.S. Cl.
CPC ............ *A61B 3/102* (2013.01); *A61B 3/1173* (2013.01); *A61B 3/12* (2013.01); *A61B 3/1208* (2013.01);
(Continued)

(58) Field of Classification Search
CPC ......... A61B 3/102; A61B 3/1173; A61B 3/12; A61B 3/1208; A61B 3/1216; A61B 3/14; G01B 9/02091
See application file for complete search history.

(56) References Cited

U.S. PATENT DOCUMENTS

| 2007/0081166 A1 | 4/2007 | Brown et al. | |
| 2011/0080561 A1* | 4/2011 | Hayashi | A61B 3/102 |
| | | | 356/511 |

(Continued)

FOREIGN PATENT DOCUMENTS

| WO | 16/127140 A1 | 8/2016 | |
| WO | 2016/127140 A1 | 8/2016 | |
| WO | WO-2016127140 A1 * | 8/2016 | ............. A61B 3/102 |

OTHER PUBLICATIONS

International Preliminary Report on Patentability in related PCT case PCT/US2019/015036 dated Jul. 28, 2020. (10 pages).

(Continued)

*Primary Examiner* — William R Alexander
*Assistant Examiner* — Sharrief I Broome
(74) *Attorney, Agent, or Firm* — Olive Law Group, PLLC (57) ABSTRACT

Optical coherence tomography (OCT) imaging systems, handhold probes, and methods that use a field curvature to match a curved surface of tissue are disclosed. According to an aspect, an OCT imaging system includes optical elements to generate diverging light. The system also includes one or more mirrors and a lens system configured to scan the diverging light onto a curved surface of an object for imaging of the object.

26 Claims, 8 Drawing Sheets

(51) Int. Cl.
*A61B 3/14* (2006.01)
*G01B 9/02091* (2022.01)
*A61B 3/117* (2006.01)

(52) U.S. Cl.
CPC .............. *A61B 3/1216* (2013.01); *A61B 3/14* (2013.01); *G01B 9/02091* (2013.01)

(56) References Cited

U.S. PATENT DOCUMENTS

| | | | |
|---|---|---|---|
| 2011/0211162 A1 | 9/2011 | Thibos et al. | |
| 2011/0299034 A1 | 12/2011 | Walsh et al. | |
| 2012/0026462 A1 | 2/2012 | Uhlhorn et al. | |
| 2012/0092615 A1* | 4/2012 | Izatt | A61B 3/102 351/205 |
| 2012/0184846 A1* | 7/2012 | Izatt | A61B 5/055 356/479 |
| 2012/0321822 A1 | 12/2012 | Li | |
| 2013/0321822 A1* | 12/2013 | Vogler | G01B 9/02091 356/497 |
| 2014/0024949 A1* | 1/2014 | Wei | G02B 21/367 600/476 |
| 2015/0342460 A1* | 12/2015 | Izatt | G01B 9/02089 600/425 |
| 2016/0367134 A1 | 12/2016 | Su | |

OTHER PUBLICATIONS

PCT Search Report and Written Opinion for PCT International Patent Application No. PCT/US19/15036, dated Apr. 26, 2019.

\* cited by examiner

OPTICAL COHERENCE TOMOGRAPHY IMAGING SYSTEMS, HANDHELD PROBES, AND METHODS THAT USE A FIELD CURVATURE TO MATCH A CURVED SURFACE OF TISSUE

CROSS REFERENCE TO RELATED APPLICATION

This application claims priority to U.S. Patent Application No. 62/621,078, filed Jan. 24, 2018, and titled SCANNER FOR OPHTHALMIC OCT AND HAND-HELD OCT ANGIOGRAPHY AND METHODS OF MAKING AND USING SAME, the content of which is incorporated herein by reference in its entirety.

FEDERALLY SPONSORED RESEARCH OR DEVELOPMENT

This is a 371 national stage patent application, which claims priority to PCT International Patent Application No. PCT/US2019/015036, filed Jan. 24, 2019, and titled OPTICAL COHERENCE TOMOGRAPHY IMAGING SYSTEMS, HANDHELD PROBES, AND METHODS THAT USE A FIELD CURVATURE TO MATCH A CURVED SURFACE OF TISSUE, which claims priority to U.S. Patent Application No. 62/621,078, filed Jan. 24, 2018, and titled SCANNER FOR OPHTHALMIC OCT AND HAND-HELD OCT ANGIOGRAPHY AND METHODS OF MAKING AND USING SAME; the disclosures of which are incorporated herein by reference in their entireties.

TECHNICAL FIELD

The presently disclosed subject matter relates generally to optical coherence tomography imaging. Particularly, the presently disclosed subject matter relates to the ergonomic design of hand-held optical coherence tomography imaging systems and methods to improve the optical performance of such systems and imaging systems in general by using scanning configurations to match the curvature of the imaged surface. The disclosed subject matter also relates to the design of ergonomic handheld OCT systems that can improve stability, operator comfort, and facilitate rapid imaging.

BACKGROUND

Optical coherence tomography (OCT) is a non-invasive imaging modality that enables in vivo cross-sectional structural imaging of living biological tissues with micron scale resolution. Due to these characteristics, OCT has become the clinical standard of care for diagnosis and monitoring of adult retinal diseases. However, most OCT systems are tabletop systems which require a compliant, seated subject. These systems are difficult if not impossible to use on noncompliant or supine subjects, such as bedridden patients, patients undergoing surgery in the operating room, and young children or infants. Handheld OCT (HH-OCT) systems have been used to bring point of care imaging to these important patient population, but they may be heavy and awkward to align, stabilize, and use. Of particular interest have been infants born at risk for blinding disease such as retinopathy or prematurity (ROP), which can progress rapidly with pathology changing from week to week. While longitudinal bedside imaging in the intensive care nursery (ICN) can provide valuable diagnostic information about the progression of the disease state, the constraints of the ICN environment such as space-restricted neonatal incubators further motivates the use of compact handheld probes.

OCT angiography (OCTA) is a functional extension of OCT that employs changes in speckle caused by blood flow as an endogenous contrast agent to image retinal microvasculature. Unlike fluorescein angiography (FA), the current gold standard for retinal vascular imaging, OCTA does not require the injection of an exogenous contrast agent and provides higher resolution, depth resolved images of the retinal vasculature. OCTA imaging of retinal diseases in adults and older children is an area of active research in ophthalmology and has provided insight into the pathogenesis of many retinal diseases including age-related macular degeneration, glaucoma, and diabetic retinopathy. While pediatric disease such as ROP have a vascular pathogenesis and occur during a period of rapid retinal vascular growth, most OCTA systems are table top systems that cannot not be easily used image infants in a supine position. These systems have been used to image infants, but require removing the infant from the incubator, holding the infant up to the chin rest, and topical anesthesia with use of a lid speculum. Armature mounted OCTA systems (Spectralis Flex Module, Heidelberg Engineering, Heidelberg, Germany) has been used recently to image supine patients and children during exams under anesthesia (EUAs) but these systems are difficult to align on a non-cooperative subject. The development of a handheld OCTA (HH-OCTA) system can enable point of care, longitudinal OCTA imaging and allow for new insights into retinal vascular development and pediatric retinal diseases. Towards this goal several groups have developed and disclosed HH-OCTA systems. These systems include a contact system used to image infants during EUAs or after surgery, two non-contact OCT systems that have been used to image adult subjects, and a handheld probe designed to image the oral mucosa.

In view of the foregoing, there is a need for improved OCT imaging systems and methods, particularly those directed to imaging the eyes of noncompliant or supine subjects.

BRIEF DESCRIPTION OF THE DRAWINGS

Having thus described the presently disclosed subject matter in general terms, reference will now be made to the accompanying Drawings, which are not necessarily drawn to scale, and wherein:

SUMMARY

The presently disclosed subject matter relates to optical coherence tomography (OCT) imaging systems, handhold probes, and methods that use a field curvature to match a curved surface of tissue. According to an aspect, an OCT imaging system includes optical elements to generate diverging light. The system also includes one or more mirrors and a lens system configured to scan the diverging light onto a curved surface of an object for imaging of the object.

The presently disclosed subject matter also relates to the design of ergonomic handheld imaging systems for imaging of supine subjects. According to an aspect, an OCT system includes optomechanics that provide the housing for optical elements and in the case of a handheld probe allow the imager to hold the probe. The optomechanics were specifically designed for the ergonomics of supine imaging and include a light weight symmetric design, ergonomic tapered tip, and an adjustable hand brace for stabilization. According to an aspect, an OCT imaging probe includes optical elements to generate diverging light. The probe also includes one or more mirrors and a lens system configured to scan the diverging light onto a curved surface of an object for imaging of the object. The probe also includes a body defining a tip and an interior that contains the OCT system. The tip defines an opening through which light from the OCT system passes.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

Regarding the terms "4F" and "5F" referenced herein, "F" refers to focal length. For example, the length of a 4F system is 4 times or about 4 times longer than the focal length of the lenses that make up the system. The lenses (or lens pairs) in these systems may or may not have equal focal lengths. If the focal lengths are unequal it is general understood that the total length of a 4F system is the sum of twice the focal length of the first lens and twice the focal length of the second lens.

Regarding the term "5F" referenced herein. "5F" refers to the approximate length of the relay telescope used in the described system. As the lens pairs used in this telescope may not have equal focal lengths the length of the particular telescope is the sum of three times the focal length of the first lens and twice the length of the second lens. While the specific device uses a 5F design, the principal of using non-collimated light and a non-4F relay telescope can be applied to the design of OCT systems and imaging systems in general. Different degrees of diverging light and relay telescope lengths can provide different degrees of curvature correction.

It is noted that traditional OCT systems use scanners use a relay telescope (an optical system to image the scanning mirrors into the pupil) that is 4F long. Unlike the systems described below a 4F systems uses collimated (non-diverging) light on the scanners.

In accordance with embodiments of the present disclosure, an OCT imaging system is provided that includes a lens system that utilizes diverging light on the scanner and a longer relay telescope to provide correction for the curvature of the image surface. The lens system may receive light from scanning mirrors and focus the received light onto a curved surface of an eye. As an example, the curved surface may be the curved surface of a retina. The lens system may also receive light that is scattered or reflected from the curved surface. Further, the lens system may have a field curvature that entirely or at least substantially matches the curved surface of the eye. The OCT imaging system may also include a detector configured to detect the light reflected from the eye.

Figure 1:
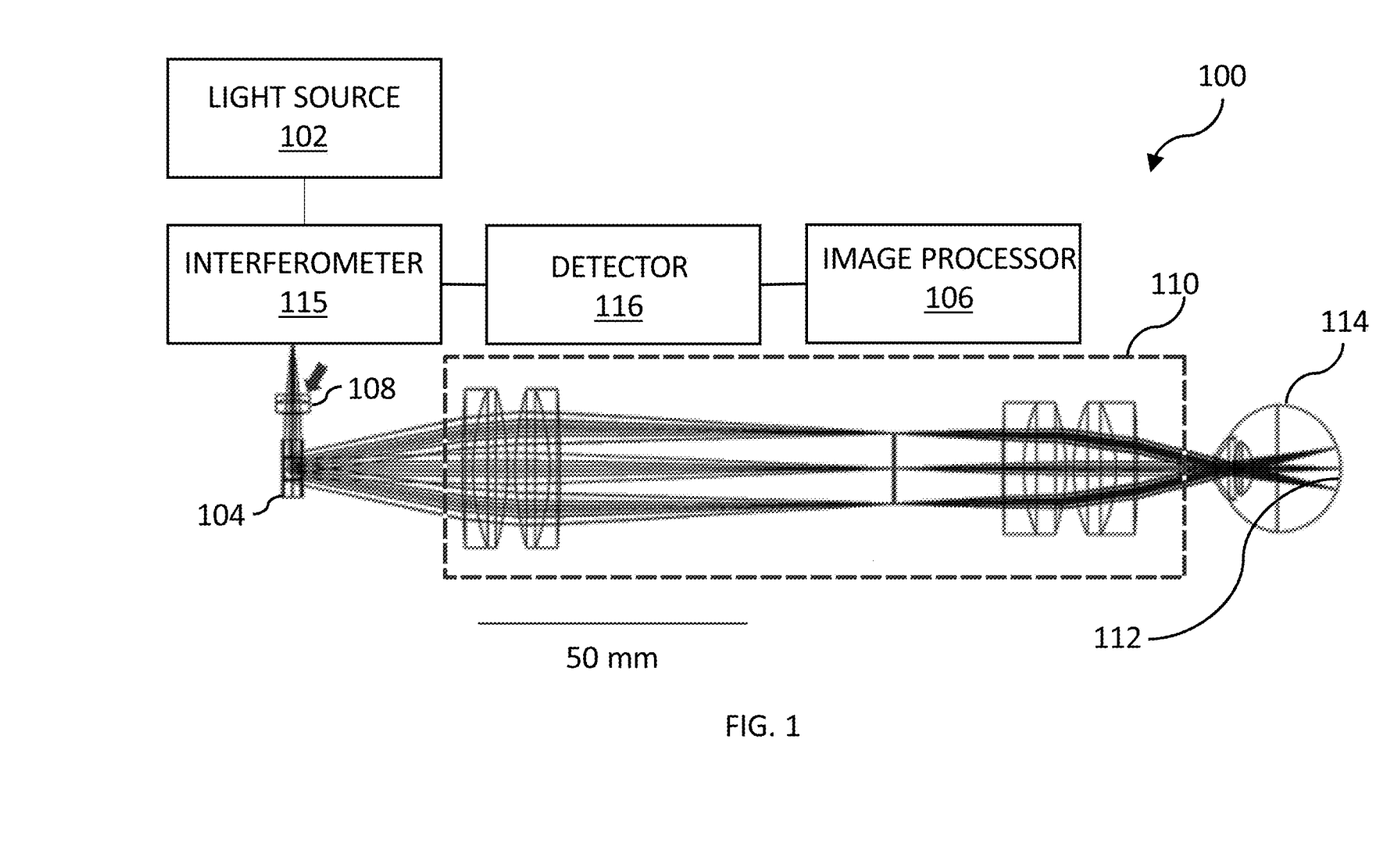
FIG. 1 is a diagram of an example OCT imaging system in accordance with embodiments of the present disclosure.

OCT imaging systems and methods disclosed herein can provide improved optical performance and can increase the diffraction limited field of view. In accordance with embodiments, OCT imaging systems disclosed herein employs diverging light on scanners, and an approximately 5F, relay telescope to image the scanners into the pupil. FIG. 1 illustrates a diagram of an example OCT imaging system 100 in accordance with embodiments of the present disclosure. Referring to FIG. 1, the diverging light on the scanner induces field curvature in the intermediate image plane. Once imaged onto the retina, the additional field curvature creates a retinal image plane that matches or closely matches the curvature of the retina (see e.g., FIG. 2).

The system 100 includes a light source 102 and a pair of orthogonal galvanometers (scanning mirrors) 104. The light source 102 may be a laser or any other suitable light source. Alternative to a pair of mirrored galvanometers, any suitable electromechanical actuator may be used for turning mirrors for angularly scanning light received from the light source 102. The scan range of a mirror may be about 28 degrees or any other suitable angle up to 100 degrees. The galvanometers (scanning mirrors) 104 may provide a scanning high scanning speed of between 250-500 Hz for B-scans suitable for OCTA.

An image processor 106 may be operatively connected to the light source 102 for controlling its operation. The image processor 106 may include suitable hardware, software, firmware, or combinations thereof for implementing the functionality disclosed herein. For example, the image processor 106 may include memory and one or more processors.

A fiber optic may be configured and suitably connected to direct light generated by the light source 102 towards a collimating lens 108. Thus, the fiber optic may provide a pathway for the light. The collimating lens 108 is positioned and operably connected to the fiber optic or otherwise suitably connected to the light source 102 for receiving the generated light and for collimating the light upstream from the galvanometers 104 where the light is scanned. The distance between the tip of the fiber optic and the collimating lens 108 may be increased to be greater than the back focal length of the collimating lens to produce diverting light on the scanner.

Downstream from the galvanometers 104, a lens system forming the 5F relay telescope 110 receives light from the galvanometers 104. The lenses of the 5F relay telescope in 110 (and relay telescopes in general for OCT) image the scanning galvanometers into the pupil of the subject's eye. The optics of the subject's eye 114 focus the scanned light creating the OCT scan. In this example, the curved surface 112 is the eye's retina. The lens system 110 and the placement of the collimating lens 108 is configured with a field curvature to match or closely match the curved surface 112. The light focused on the retina is scattered or reflected back towards the lens system 110 and collected by an interferometer 115.

The system 100 includes a detector 116 configured to process a signal to generate an image of the eye 114, particularly the retina. The interferometer 115 may be configured to generate a detectable optical signal by interfering light backscattered from the sample to light from a fixed reference delay. The detector 116 may generate a depth resolved, output signal representative of the image of the eye 114. The image processor 106 may receive the output signal from the detector 116 and generate an image of the eye for display to a user of the system 100. For example, the image processor 106 may use a suitable display to display the image.

Figure 2:
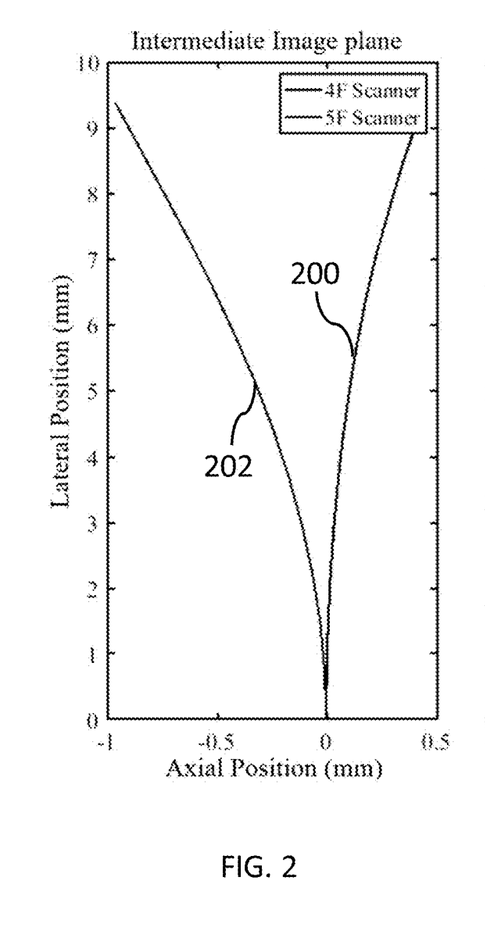
FIG. 2 is a graph showing example curvature of an intermediate image plane for a 4F scanner and a system having a 5F configuration in accordance with embodiments of the present disclosure.

FIG. 2 is a graph showing example curvature of an intermediate image plane for a 4F scanner and a system having a 5F configuration in accordance with embodiments of the present disclosure. Referring to FIG. 2, line 200 shows the curvature for a 4F scanner, and line 202 shows the curvature for a system having the 5F configuration, such as the system 100 shown in FIG. 1.

Figure 3:
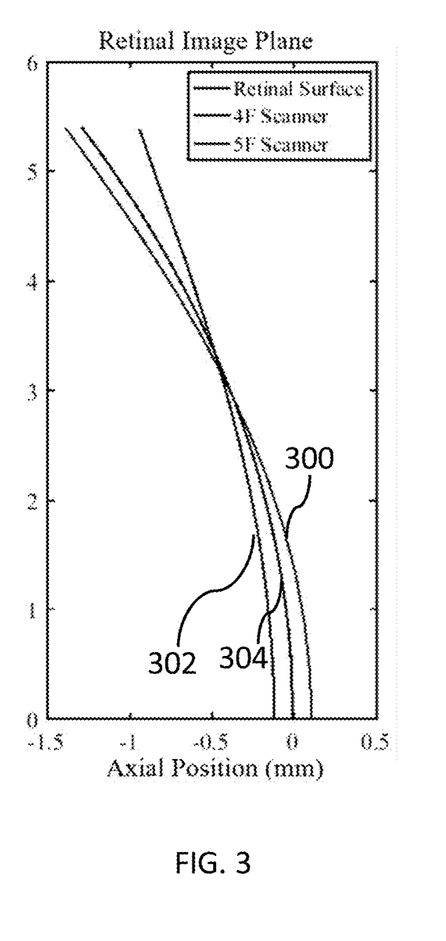
FIG. 3 is a graph showing example curvature of a retinal image plane for a 4F scanner and a system having a 5F configuration in accordance with embodiments of the present disclosure.

FIG. 3 is a graph showing example curvature of a retinal image plane for a 4F scanner and a system having a 5F configuration in accordance with embodiments of the present disclosure. Referring to FIG. 3, line 300 shows the curvature for a system having the 5F configuration, such as the system 100 shown in FIG. 1. Line 302 shows the curvature for the 4F scanner. Line 304 shows the curvature of the retinal surface.

Lenses of an OCT imaging system in accordance with embodiments of the present disclosure may be lenses provided by suitable lens manufacturers such as Edmund Optics Inc. of Barrington, N.J. and Thorlabs, Newton, N.J. Simulation of the functionality of such lenses may be implemented using ray tracing software such as software provided by Radiant Zemax LLC of Redmond, Wash. and by use of the Goncharov and Dainty eye model, an eye model for non-wide field systems. An OCT imaging system having a 5F configuration as disclosed herein can produce diffraction limited spots over a ~30° field of view (limited by clipping on a lens aperture).

Figure 4:
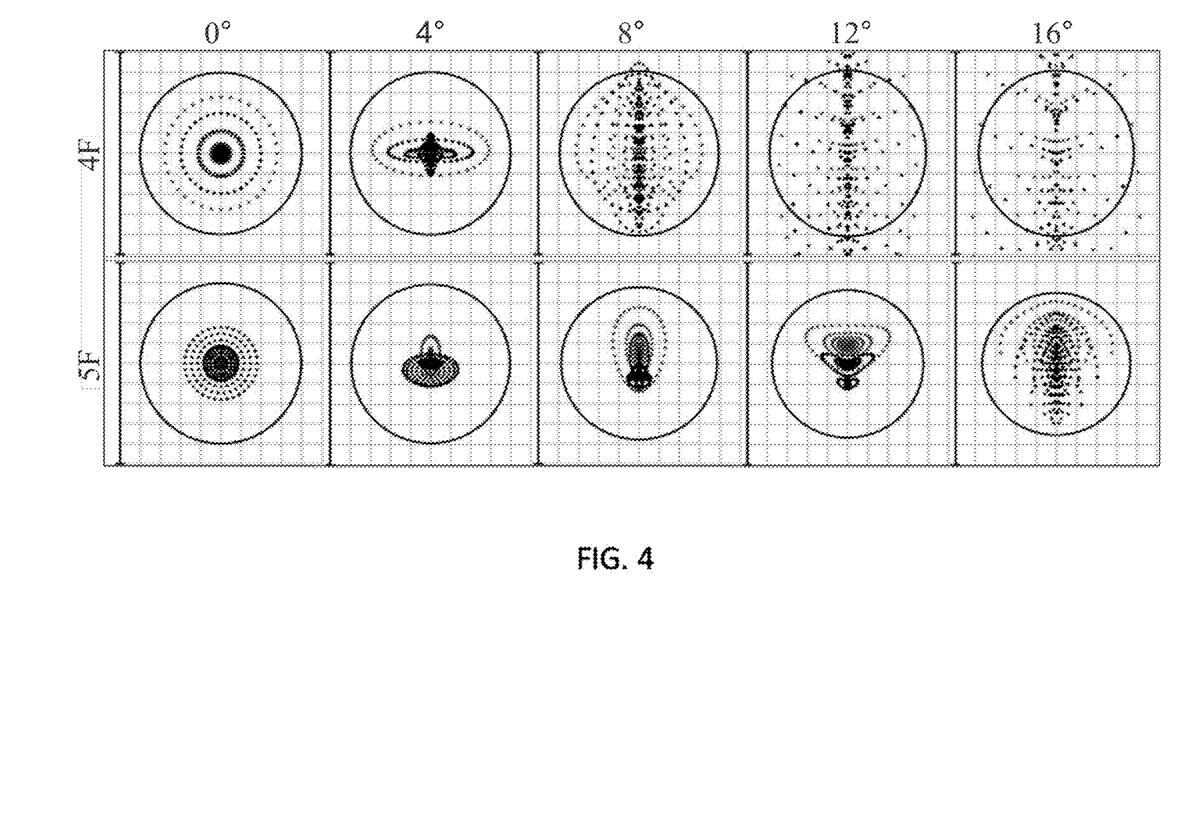
FIG. 4 are simulated spot diagrams (Zemax) for a 4F scanner and an OCT imaging system having a 5F configuration in accordance with embodiments of the present disclosure.

FIG. 4 are Zemax spot diagrams for a 4F scanner and an OCT imaging system having a 5F configuration in accordance with embodiments of the present disclosure. Referring to FIG. 4, the 4F scanner diagrams are shown in the top row, and the 5F scanner diagrams are shown in the bottom row. These are shown as a function of angle (measured as the angle between the chief ray and the optic axis in the eye). The circle denotes the airy radius (12.0 micrometers for both systems at 0 degrees). Diffraction limited performance can be achieved if all of the simulated rays fall within the airy radius.

In accordance with embodiments, OCT imaging systems, such as system 100 shown in FIG. 1, may be integrated into a probe. The probe may have a housing that defines an interior for holding the galvanometers 104 and lens system 110 shown in FIG. 1.

Figure 5A:
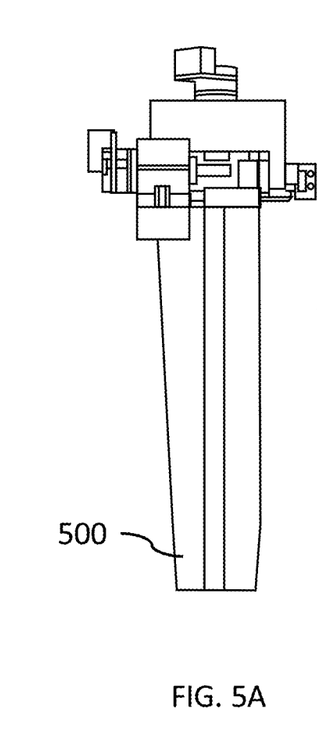
FIGS. 5A-5E are renderings of an example OCT probe in accordance with embodiments of the present disclosure.
Figure 5B:
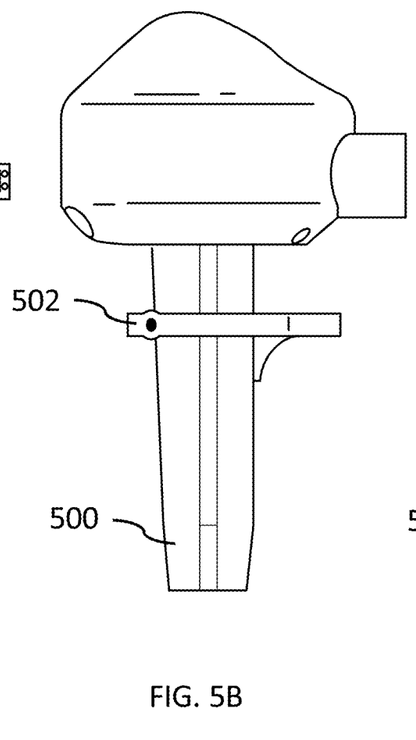
Figure 5C:
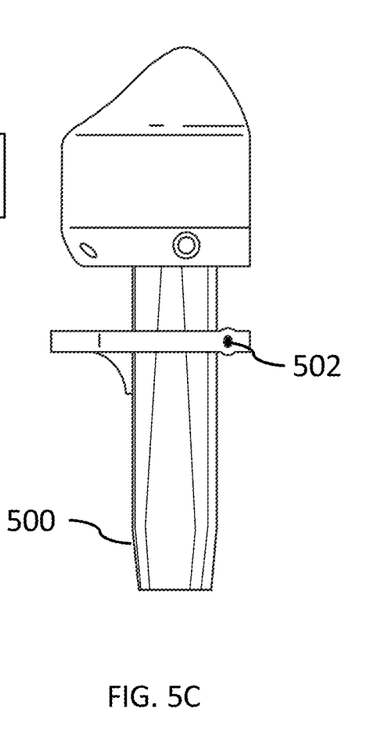

FIGS. 5A-5C are images of an example OCT probe in accordance with embodiments of the present disclosure. Particularly, the figures show a probe that implements OCTA. Since OCTA uses changes in speckle caused by the motion of flowing blood as a source of contrast, it can be susceptible to other sources of motion causing the OCTA signal to wash out. This is most often seen when saccades cause bright streaks on OCTA images. For hand-held OCTA, operator hand motion adds another potential source of signal corruption. To minimize this effect, the ergonomics of the probe shown in FIGS. 5A-5C have been designed to match the probe tip grip that operators have been observed to prefer. Operators can use their free hand to brace the probe on the subject's forehead or cheek and open a subject's eye (e.g., infant's eye) with or without the use of an eyelid speculum. This braced position can simplify alignment of the probe with the pupil and maintaining the correct working distance. The probe was designed to be as symmetric as possible with a tapered tip 500. Additionally, the probe includes an optional adjustable stabilization brace 502 to provide the operator with a point of contact that was closer to the center of mass of the probe and can be adjusted to optimize for the size of the operator's hand and specific grip required for a given imaging environment. The collimating lens (e.g., the collimating lens 108 shown in FIG. 1) may be placed on a motorized stage (e.g., a motorized stage provided by National Aperture Inc., of Salem, N.H.) to allow for +10 D to −10 D refractive error correction. Undersized dowel pins and custom retaining rings may be used to provide for precise positioning of mechanical and optical elements, respectively. The optomechanics were machined, by use of computer numerical control (CNC) equipment, from aluminum while the enclosure and brace were 3D printed from high durability plastic (e.g., plastic available from Formlabs, Somerville, Mass.). The complete, assembled probe weighs 700 g and has a form factor of approximately 22×10×14 cm.

Figure 5D:
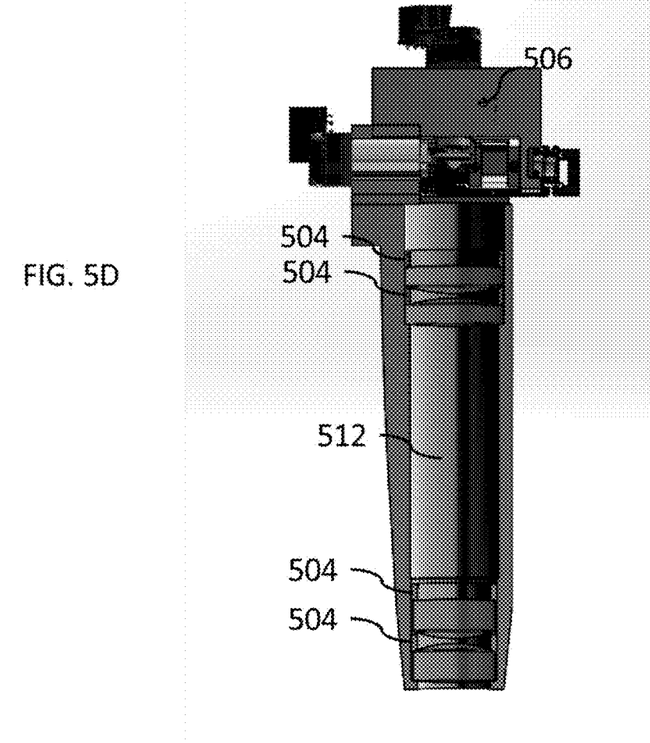
Figure 5E:
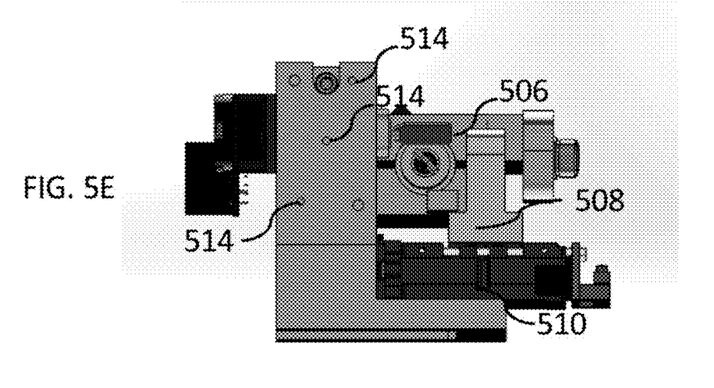

FIG. 5D is a front, cross-sectional view of the OCT probe shown in FIGS. 5A-5C showing the internal components of the relay telescope 512. FIG. 5E is a drawing of the galvanometer block 506 without the relay telescope. Referring to FIGS. 5D and 5E, the lens tube and galvanometer block 506 and collimating lens sub-assembly 508 are shown. Tangential retaining rings 504 were provided to ensure precise positioning of optical elements. The galvanometer block and lens tube are mated using undersized dowel pins 514 to provide precise alignment between the two parts. The collimating lens assembly 508 was placed on a motorized stage 510 to allow for digitally controlled +10 D to −10 D refractive error correction. The use of a short focal length lens as the collimating lens 108 allowed the combined galvanometer block and collimating lens assembly to be as compact, lightweight, and symmetric as possible. The mechanics of the OCT probe shown in this example were designed in SolidWorks (Dassault Systémes SolidWorks Corp., Concord, Mass.). To ensure both lightweight and high precision the optomechanics were CNC machined from 6061 aluminum alloy and toleranced to 0.0002 inches. The retaining rings were machined from brass to prevent bonding between the retaining rings and the aluminum optomechanics. The enclosure and brace were 3D printed from high durability plastic to provide an impact resistance case that protects the optics of the system.

In an example, an OCT imaging system in accordance with the present disclosure may be an HH-OCTA system. The light source (e.g., light source 102 shown in FIG. 1) may be a 200 kHz, 1060 nm swept source laser (such as a laser available from Axsun Technologies Inc., of Bilerica, Mass.) illuminating a Mach-Zhender interferometer (e.g., interferometer shown in 115). The interferometric signal may be detected with a 1 GHz dual balanced receiver (Thorlabs, Inc., of Newton, N.J.), and digitized using a 1.8 GS/s digitizer (Alazar Technologies Inc., Pointe-Claire, Quebec) (e.g., the detector 106 shown in FIG. 1). Graphics processing unit (GPU)-based software (e.g., residing on image processor 106 of FIG. 1) may be used to perform real time processing, display, and rendering of OCT data. Structural OCT imaging in the ICN may be performed with a 950 A-scans/B-scan, 128 2× averaged B-scans/volume imaging protocol (1.36 s total acquisition time) over a 10×10 mm field of view. HH-OCTA imaging may be performed with two protocols: a faster 300 A-scan/B-scan, 4 repeated B-scans, 300 lateral locations sampled (2.5 s acquisition time) protocol and a wider field of view 500 A-scan/B-scan, 4 repeated B-scan, 500 lateral locations sampled (6.0 s acquisition time) protocol. The repeated B-scans were registered using phase correlation, OCTA was generated using speckle variance, and graph search based segmentation was used to delineate retinal layers in order to create layer-specific enface projections of the retinal vasculature. Segmentation was manually corrected by an expert grader for subjects in which pathology was present. The inner plexiform layer (IPL) was used as the boundary between the SVC and DVC and used to create projections of the respective vascular complexes. Corrections to reference arm delay and lateral scan dimension to account for the shorter length of the infant eye were applied.

In experiments, an OCT imaging system in accordance with the present disclosure was used for HH-OCT and HH-OCTA imaging. This imaging was performed, in one experiment, in 7 awake adult volunteers, 9 infants and young children during EUAs, and 30 infants in the ICN or during follow up clinic visits, with or without pharmacological dilation as clinically indicated. During EUAs, FA imaging (Retcam3, Natus Medical Incorporated, Pleasanton, Calif.), was performed as a routine part of care. Total imaging time was limited to 15 minutes for each subject. Optical power was set to less than 1.8 mW on the cornea, less than the ANSI Z136.1 standard for 1060 nm light.

The high speed and the ergonomic grip and the optional adjustable, stabilization brace of the HH-OCTA probe (such as shown in FIGS. 5A-5C) can facilitate regular structural OCT imaging in the ICN and other challenging imaging environments. During imaging, the probe may be positioned vertically above the eye of the subject with the imager holding the probe by the tip (e.g., tip 500 shown in FIGS. 5A-5C). The imager's other hand may rest on the forehead of the subject to thereby brace the probe and gently hold the subject's eyelids open. The symmetric design of the probe, lack of additional components, and hand brace facilitate imaging in this manner. Over 68 imaging sessions (across 30 different subjects) in the ICN and clinic, the HH-OCTA probe was able to capture structural images of the optic nerve and fovea 98.5% of the time.

Figure 6:
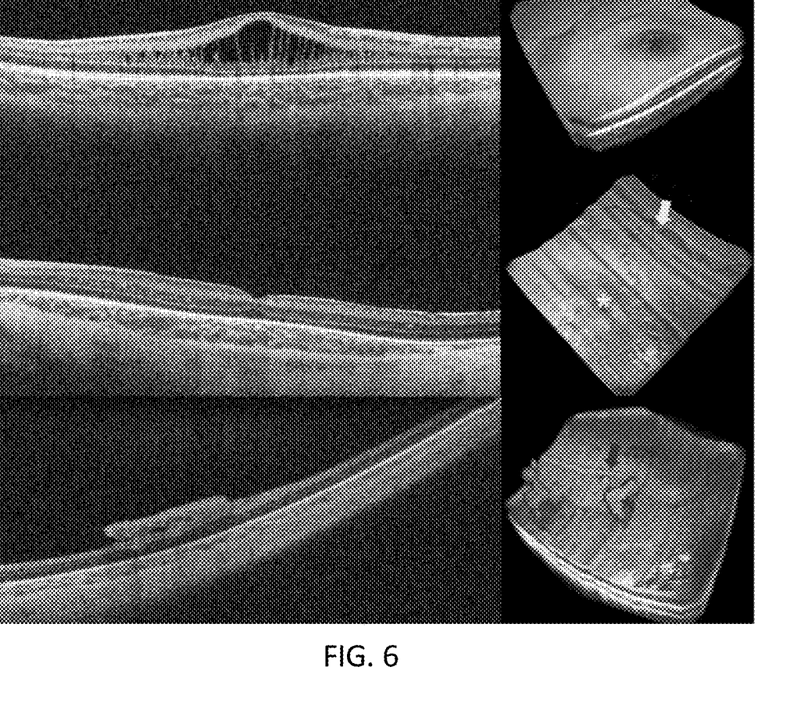
FIG. 6 are selected B-scans and volume renders of a retina from research HH-SSOCT imaging of non-sedated infants.

Selected volume renders and B-scans from ICN imaging are shown in FIG. 6, which are selected B-scans and volume renders of a retina from research HH-SSOCT imaging of non-sedated infants. These images demonstrate the ability of the probe to capture clinically relevant features including the foveal depression, cystoid macular edema of prematurity, and peripheral preretinal neovascular elevations in an infant with ROP. Turning to FIG. 6, image labeled "a" shows a premature-born infant imaged one week after estimated date of term birth. In image "a," a cystoid macular edema elevates the central macula, which is identified with a star. In the image labeled "b," it shows a premature infant retina imaged weeks before estimated date for term birth, and the fovea has a normal depression without edema, which is identified with a star. But in image "b," there are engorged blood vessels on the surface of the retina as shown by the arrow. Image labeled "c" shows peripheral views from the same infant and reveals preretinal neovascular elevations (indicated by the star) and a ridge at the vascular/avascular junction (indicated by the arrow). All images shown in FIG. 6 were acquired at 950 A-scans/B-scan, 2× registered and averaged B-scans, and 128 B-scans/volume. While features like preretinal neovascular elevations are visible in cross-sectional imaging, the 3D context provided by volumetric imaging allows for better visualization of 3D structures such as engorged blood vessels, the extent and composition of preretinal neovascular tissues, and structural changes at the vascular/avascular junction in infants with ROP.

The high speed in general and the ergonomic grip of the probe in particular enable high quality OCTA imaging. Since OCTA is motion sensitive stabilization of the handheld probe is far more important for OCTA than regular structural OCT imaging. Compared to other research handheld OCTA probes reported in the scientific literature that do not feature an ergonomic design, this is the only system capable of providing OCTA images with quality comparable to large table top systems and the only handheld OCTA system that has been used on non-sedated infants.

Figure 7:
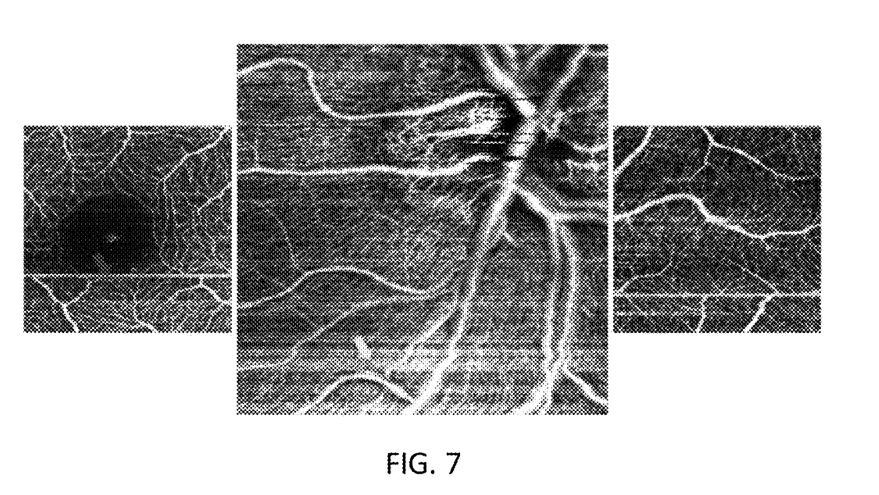
FIG. 7 are representative OCTA images from a healthy adult.

Initial HH-OCTA imaging to assess the OCTA capabilities of the system was performed in healthy adult volunteers lying in a supine position. These images are shown in FIG. 7, which are representative OCTA images from a healthy adult. The left image of FIG. 7 shows an ~1.5×1.5 mm angiogram of the fovea showing the foveal avascular zone with well-demarcated capillaries at the margin. The center image of FIG. 7 shows an ~3×3 mm angiogram of the optic nerve head showing multiple levels of large to small vessels of the optic nerve head (upper right corner) and retina. The right image of FIG. 7 shows an ~1.5×1.5 mm angiogram of nasal retina. The arrows shown in the left and right images of FIG. 7 denote the location of artifacts caused by saccades, while the arrow in the middle image of FIG. 7 denotes the location of artifacts caused by operator hand motion. These images show clear visualization of the capillaries forming the FAZ, peripapillary vasculature emerging radially from the optic disc, and retinal capillaries in a nasal to the optic disc. These images also demonstrate the difference between artifacts caused by saccades and hand motion. Saccades manifests as narrow streaks on the angiograms with sharp discontinuities between the vasculature on each side of the artifact (shown by the arrows in the left and right images of FIG. 7). Throughout the OCTA images presented in this paper there are broader but less corrupted artifacts with wavy but continuous vasculature (shown by the arrows in the left and right images of FIG. 7). Due to their presence in images of cooperative, fixating adults, it is believed that these artifacts result from washout of the OCTA signal caused by the operator's hand motion causing bulk decorrelation of the background tissue.

Figure 8:
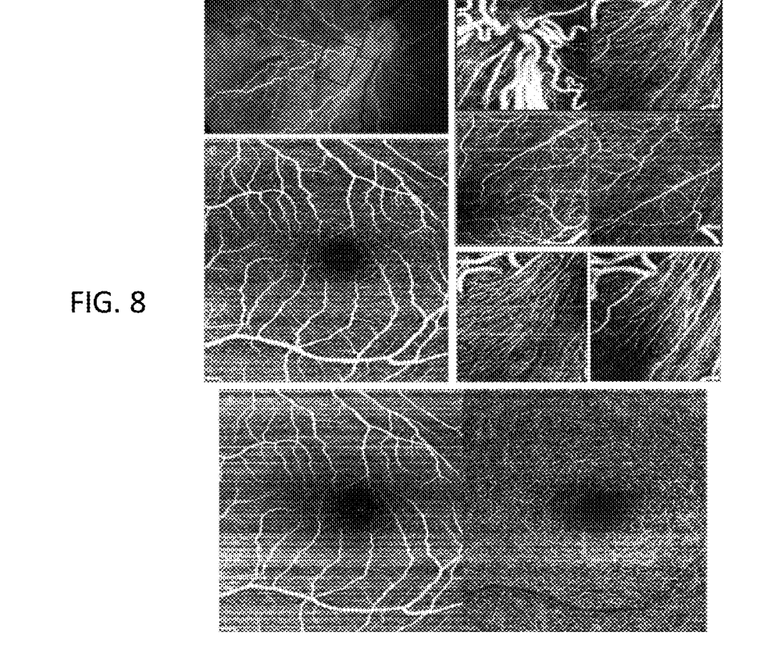
FIG. 8 are images that show a comparison of FA to HH-OCTA during EUA.

HH-OCTA imaging was performed in children and infants during EUAs. FIG. 8 illustrates images that show a comparison of FA to HH-OCTA during EUA. The image labeled "a" of FIG. 8 shows FA from an infant with a history of ROP. The boxes in image "a" denote the location of the corresponding HH-OCTA scans. Images label "b" in FIG. 8 shows HH-OCTA from the optic nerve, peripapillary region, perifoveal region, and the edge of the fovea. Also, images labeled "b" were taken with 300 A-scans/B-scan, 4 repeated B-scans, and 300 lateral locations sampled per volume. The image labeled "c" shows a wider field HH-OCTA of a child undergoing EUA due to a family history of familial exudative vitreoretinopathy. Images were taken with 500 A-scans/B-scan, 4 repeated B-scans, and 500 lateral locations sampled per volume. The image labeled "d" is a peripapillary image from image "b" split into superficial and deep layers. Image "e" is an image from image "c" split into SVC and DVC. When compared to FA HH-OCTA offers depth resolved visualization of capillary level vasculature that is not visible on FA without the need for intravenous injection of a contrast agent. In a young child with a history of retinopathy of prematurity (ROP), OCTA shows the tortuous microvasculature vasculature in multiple regions of the retina with the fovea dragged inferotemporally to the near periphery. Separating the retinal microvasculature into by depth reveals a network of stretched superficial vessels lying on top of deeper, larger vessels. Since the IPL is not visible due to the presence of thickened inner retina and the peripheral retinal location, 40% of the ILM to RPE thickness was chosen as the boundary between the superficial and deep vascular layers (See image "d" of FIG. 8). In another child undergoing EUA due to a family history of familial exudative vitreoretinopathy (FEVR) HH-OCTA shows a regular vascular microvascular pattern including the foveal avascular zone (image "c" of FIG. 8). Separating the image into the SVC and DVC again reveals normal vascular patterns (image "e" of FIG. 8).

Figure 9:
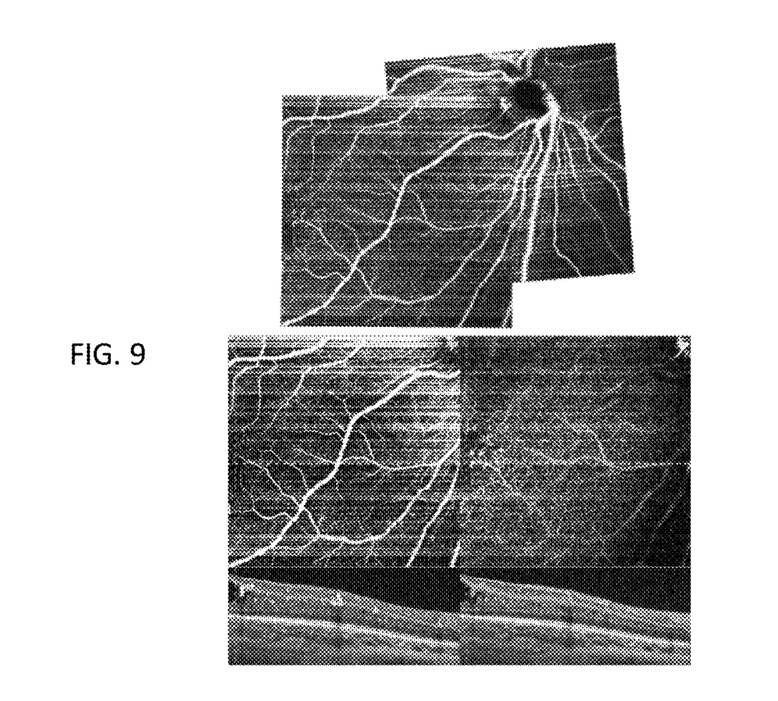
FIG. 9 are HH-OCTA images showing the peripapillary and macular microvasculature in the nasal macula.

While the development of retinal abnormalities such as cystoid macular edema and preretinal neovascular elevations characteristic of ROP can be seen with structural OCT (see e.g., FIG. 6), the vascular structure and development of these abnormalities is largely unknown. A 41 PMA infant with a history of ROP and cystoid macular edema was imaged during a follow up visit in the clinic. For example, FIG. 9 are HH-OCTA images showing the peripapillary and macular microvasculature in the nasal macula. The top image of FIG. 9 shows overlaid angiograms of the optic nerve head, peripapillary vasculature, and the edge of the fovea. The star denotes the edge of the fovea. The bottom images of FIG. 9 show the peripapillary/foveal angiogram of SVC (left image) and DVC (right image). A selected B-scan with and without OCTA flow superimposed are shown below the angiogram. The horizontal dashed line in the left image denote the location of the selected B-scan. The vertical dashed lines in the right image denotes the same lateral location on the angiograms and selected B-scans. A line on the B-scans denotes the manually corrected IPL. Images were taken with 500 A-scans/B-scan, 4 repeated B-scans, and 500 lateral locations sampled per volume. Near the edge of the fovea and within the region of cystoid macular edema there are several bulb-like vascular terminations, which may represent micro-aneurysms, small vascular loops, or other microvascular abnormalities. The OCTA B-scan, SVC projection, and DVC projection reveal that these loops are in the DVC and within the area of cystoid macular edema. HH-OCTA images of preretinal neovascular elevations were obtained from a 41 week PMA infant (separate structural images shown in image "c" of FIG. 6) who subsequently underwent peripheral laser treatment (see FIG. 10).

Figure 10:
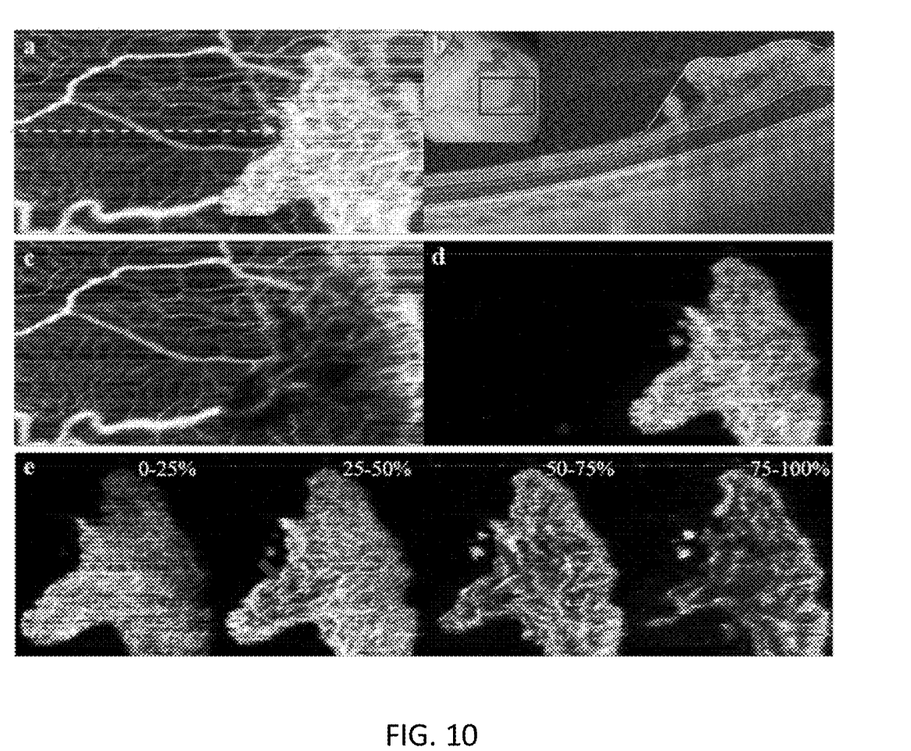
FIG. 10 shows images of vascular structure of a preretinal neovascular elevation.

FIG. 10 shows images of vascular structure of a preretinal neovascular elevation. a) OCTA image of all retinal vasculature. Lines in FIG. 10 denote the location of the B-scan shown in the image labeled "b". Image "b" shows selected B-scan with manually corrected segmentations. One surface is of the retina including the neo-vascular plaque, another surface is of the retina excluding the neo-vascular plaque, another surface is the IPL, and another surface is of the RPE. The image labeled "c" is the OCTA of the vasculature excluding the neo-vascular plaque. The image labeled "d" is of the OCTA of the neo-vascular plaque. The image labeled "e" is of the neo-vascular plaque divided into slices that are 25% of the total thickness of the plaque. The arrow denotes the location of the "trunk" within the neovascular plaque. The angiograms show the vascular connection of the neovascular elevation to the retinal vasculature. While FA typically shows the neovascular elevations as a single, bright structure, the depth resolved OCTA images reveal the internal vascular structure of the neovascular elevation; a "trunk" of larger vessels deeper in the neovascular elevation connects the retina to a dense network of finer vasculature closer to the surface of the elevation.

Systems and methods disclosed herein include a unique, ergonomic, 200 kHz HH-OCTA probe optimized for supine non-contact imaging. The probe weighs about 700 g, has −10D to +10D refractive error correction, ergonomic design, stabilization brace, and a 30° diffraction limited field of view. Using a model in experiments, HH-OCTA imaging was performed in healthy adult volunteers, pediatric patients undergoing exams under anesthesia, and infants in the ICN/clinic. The OCTA images reported in this manuscript are the first HH-OCTA taken of non-sedated infants and the first HH-OCTA images to show depth-resolved retinal microvasculature and microvascular abnormalities. These images show vascular abnormalities in close proximity to pathological structures and it is believed that further imaging with this probe can lead to new insights into the development and pathology of the pediatric retina.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

REFERENCES

1. D. Huang, E. A. Swanson, C. P. Lin, J. S. Schuman, W. G. Stinson, W. Chang, M. R. Hee, T. Flotte, K. Gregory, 1. and C. A. Puliafito, "Optical coherence tomography," science 254, 1178-1181 (1991).
2. E. A. Swanson, J. Izatt, C. Lin, J. Fujimoto, J. Schuman, M. Hee, D. Huang, and C. Puliafito, "In vivo retinal imaging by optical coherence tomography," Optics letters 18, 1864-1866 (1993).
3. J. S. Schuman, C. A. Puliafito, J. G. Fujimoto, and J. S. Duker, *Optical coherence tomography of ocular diseases* (Slack New Jersey, 2004).
4. A. C. Lee, R. S. Maldonado, N. Sarin, R. V. O'Connell, D. K. Wallace, S. F. Freedman, M. Cotten, and C. A. Toth, "Macular features from spectral domain optical coherence tomography as an adjunct to indirect ophthalmoscopy in retinopathy of prematurity," Retina (Philadelphia, Pa.) 31, 1470 (2011).
5. L. Sheck, W. I. Davies, P. Moradi, A. G. Robson, N. Kumaran, A. C. Liasis, A. R. Webster, A. T. Moore, and M. Michaelides, "Leber Congenital Amaurosis Associated with Mutations in CEP290, Clinical Phenotype, and Natural History in Preparation for Trials of Novel Therapies," Ophthalmology (2018).
6. M. I. Seider, D. S. Grewal, and P. Mruthyunjaya, "Portable optical coherence tomography detection or confirmation of ophthalmoscopically invisible or indeterminate active retinoblastoma," Ophthalmic Surgery, Lasers and Imaging Retina 47, 965-968 (2016).
7. S. H. Chavala, S. Farsiu, R. Maldonado, D. K. Wallace, S. F. Freedman, and C. A. Toth, "Insights into advanced retinopathy of prematurity using handheld spectral domain optical coherence tomography imaging," Ophthalmology 116, 2448-2456 (2009).
8. W. Jung, J. Kim, M. Jeon, E. J. Chaney, C. N. Stewart, and S. A. Boppart, "Handheld optical coherence tomography scanner for primary care diagnostics," IEEE Transactions on Biomedical Engineering 58, 741-744 (2011).
9. A. Y. Tong, M. El-Dairi, R. S. Maldonado, A. L. Rothman, E. L. Yuan, S. S. Stinnett, L. Kupper, C. M. Cotten, K. E. Gustafson, and R. F. Goldstein, "Evaluation of optic nerve development in preterm and term infants using handheld spectral-domain optical coherence tomography," Ophthalmology 121, 1818-1826 (2014).
10. A. Mallipatna, A. Vinekar, C. Jayadev, S. Dabir, M. Sivakumar, N. Krishnan, P. Mehta, T. Berendschot, and N. K. Yadav, "The use of handheld spectral domain optical coherence tomography in pediatric ophthalmology practice: our experience of 975 infants and children," Indian journal of ophthalmology 63, 586 (2015).
11. W. Bowl, M. Andrassi-Darida, K. Holve, S. Schweinfurth, R. Knobloch, and B. Lorenz, "Handheld Optical Coherence Tomography in Paediatric Ophthalmology: Experience of the Department of Ophthalmology in Giessen," Klinische Monatsblatter fur Augenheilkunde 233, 1142-1148 (2016).
12. L. Kong, M. Fry, M. Al-Samarraie, C. Gilbert, and P. G. Steinkuller, "An update on progress and the changing epidemiology of causes of childhood blindness worldwide," Journal of American Association for Pediatric Ophthalmology and Strabismus {JAAPOS} 16, 501-507 (2012).
13. R. K. Wang, S. L. Jacques, Z. Ma, S. Hurst, S. R. Hanson, and A. Gruber, "Three dimensional optical angiography," Optics express 15, 4083-4097 (2007).
14. Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt Express 20, 4710-4725 (2012).
15. A. Mariampillai, B. A. Standish, E. H. Moriyama, M. Khurana, N. R. Munce, M. K. Leung, J. Jiang, A. Cable, B. C. Wilson, and I. A. Vitkin, "Speckle variance detection of microvasculature using swept-source optical coherence tomography," Optics letters 33, 1530-1532 (2008).
16. A. Zhang, Q. Zhang, C. L. Chen, and R. K. Wang, "Methods and algorithms for optical coherence tomography-based angiography: a review and comparison," J Biomed Opt 20, 100901 (2015).
17. L. An, J. Qin, and R. K. Wang, "Ultrahigh sensitive optical microangiography for in vivo imaging of microcirculations within human skin tissue beds," Optics express 18, 8220-8228 (2010).
18. H. C. Hendargo, R. Estrada, S. J. Chiu, C. Tomasi, S. Farsiu, and J. A. Izatt, "Automated non-rigid registration and mosaicing for robust imaging of distinct retinal capillary beds using speckle variance optical coherence tomography," Biomedical optics express 4, 803-821 (2013).
19. R. F. Spaide, J. M. Klancnik, and M. J. Cooney, "Retinal vascular layers imaged by fluorescein angiography and optical coherence tomography angiography," JAMA ophthalmology 133, 45-50 (2015).
20. T. E. De Carlo, A. Romano, N. K. Waheed, and J. S. Duker, "A review of optical coherence tomography angiography (OCTA)," International Journal of Retina and Vitreous 1, 5 (2015).
21. Y. Jia, S. T. Bailey, D. J. Wilson, O. Tan, M. L. Klein, C. J. Flaxel, B. Potsaid, J. J. Liu, C. D. Lu, and M. F. Kraus, "Quantitative optical coherence tomography angiography of choroidal neovascularization in age-related macular degeneration," Ophthalmology 121, 1435-1444 (2014).
22. N. V. Palejwala, Y. Jia, S. S. Gao, L. Liu, C. J. Flaxel, T. S. Hwang, A. K. Lauer, D. J. Wilson, D. Huang, and S. T. Bailey, "Detection of non-exudative choroidal neovascularization in age-related macular degeneration with optical coherence tomography angiography," Retina (Philadelphia, Pa.) 35, 2204 (2015).
23. L. Kuehlewein, M. Bansal, T. L. Lenis, N. A. Iafe, S. R. Sadda, M. A. Bonini Filho, E. Talisa, N. K. Waheed, J. S. Duker, and D. Sarraf, "Optical coherence tomography angiography of type 1 neovascularization in age-related macular degeneration," American journal of ophthalmology 160, 739-748. e732 (2015).
24. Y. Jia, E. Wei, X. Wang, X. Zhang, J. C. Morrison, M. Parikh, L. H. Lombardi, D. M. Gattey, R. L. Armour, and B. Edmunds, "Optical coherence tomography angiography of optic disc perfusion in glaucoma," Ophthalmology 121, 1322-1332 (2014).
25. L. Liu, Y. Jia, H. L. Takusagawa, A. D. Pechauer, B. Edmunds, L. Lombardi, E. Davis, J. C. Morrison, and D. Huang, "Optical coherence tomography angiography of the peripapillary retina in glaucoma," JAMA ophthalmology 133, 1045-1052 (2015).
26. A. Yarmohammadi, L. M. Zangwill, A. Diniz-Filho, M. H. Suh, P. I. Manalastas, N. Fatehee, S. Yousefi, A. Belghith, L. J. Saunders, and F. A. Medeiros, "Optical coherence tomography angiography vessel density in healthy, glaucoma suspect, and glaucoma eyes," Investigative ophthalmology & visual science 57, OCT451-OCT459 (2016).
27. Y. Jia, S. T. Bailey, T. S. Hwang, S. M. McClintic, S. S. Gao, M. E. Pennesi, C. J. Flaxel, A. K. Lauer, D. J. Wilson, J. Hornegger, J. G. Fujimoto, and D. Huang, "Quantitative optical coherence tomography angiography of vascular abnormalities in the living human eye," Proc Natl Acad Sci USA 112, E2395-2402 (2015).
28. A. Ishibazawa, T. Nagaoka, A. Takahashi, T. Omae, T. Tani, K. Sogawa, H. Yokota, and A. Yoshida, "Optical coherence tomography angiography in diabetic retinopathy: a prospective pilot study," American journal of ophthalmology 160, 35-44. e31 (2015).
29. S. A. Agemy, N. K. Scripsema, C. M. Shah, T. Chui, P. M. Garcia, J. G. Lee, R. C. Gentile, Y.-S. Hsiao, Q. Zhou, and T. Ko, "Retinal vascular perfusion density mapping using optical coherence tomography angiography in normals and diabetic retinopathy patients," Retina 35, 2353-2363 (2015).
30. J. Chen and L. E. Smith, "Retinopathy of prematurity," Angiogenesis 10, 133-140 (2007).
31. A. Vinekar, L. Chidambara, C. Jayadev, M. Sivakumar, C. A. Webers, and B. Shetty, "Monitoring neovascularization in aggressive posterior retinopathy of prematurity using optical coherence tomography angiography," Journal of American Association for Pediatric Ophthalmology and Strabismus 20, 271-274 (2016).
32. R. J. House, S. T. Hsu, A. S. Thomas, A. P. Finn, C. A. Toth, M. A. Materin, and L. Vajzovic, "Vascular Findings In A Small Retinoblastoma Tumor Using OCT-A," Ophthalmology Retina (2018).
33. S. T. Hsu, X. Chen, H. T. Ngo, R. J. House, M. P. Kelly, L. B. Enyedi, M. A. Materin, M. A. El-Dairi, S. F. Freedman, and C. A. Toth, "Imaging infant retinal vasculature with optical coherence tomography angiography," Ophthalmology Retina.
34. J. P. Campbell, E. Nudleman, J. Yang, O. Tan, R. P. Chan, M. F. Chiang, D. Huang, and G. Liu, "Handheld Optical Coherence Tomography Angiography and Ultra-Wide-Field Optical Coherence Tomography in Retinopathy of Prematurity," JAMA ophthalmology 135, 977-981 (2017).
35. S. J. Kim, J. Yang, G. Liu, D. Huang, and J. P. Campbell, "Optical Coherence Tomography Angiography and Ultra-Widefield Optical Coherence Tomography in a Child With Incontinentia Pigmenti," Ophthalmic Surgery, Lasers and Imaging Retina 49, 273-275 (2018).
36. J. Yang, L. Liu, J. P. Campbell, D. Huang, and G. Liu, "Handheld optical coherence tomography angiography," Biomedical Optics Express 8, 2287-2300 (2017).
37. S. Shaozhen, J. Xu, Y. Li, Q. Zhang, and R. K. Wang, "Miniature hand-held OCT probe for wide-field retinal angiography for prematurity and pediatric applications," Investigative Ophthalmology & Visual Science 59, 5203-5203 (2018).
38. M.-T. Tsai, Y. Chen, C.-Y. Lee, B.-H. Huang, N. H. Trung, Y.-J. Lee, and Y.-L. Wang, "Noninvasive structural and microvascular anatomy of oral mucosae using hand-held optical coherence tomography," Biomedical optics express 8, 5001-5012 (2017).
39. F. LaRocca, D. Nankivil, S. Farsiu, and J. A. Izatt, "Handheld simultaneous scanning laser ophthalmoscopy and optical coherence tomography system," Biomedical optics express 4, 2307-2321 (2013).
40. D. Nankivil, G. Waterman, F. LaRocca, B. Keller, A. N. Kuo, and J. A. Izatt, "Handheld, rapidly switchable, anterior/posterior segment swept source optical coherence tomography probe," Biomedical Optics Express 6, 4516-4528 (2015).
41. F. LaRocca, D. Nankivil, T. DuBose, C. A. Toth, S. Farsiu, and J. A. Izatt, "In vivo cellular-resolution retinal imaging in infants and children using an ultracompact handheld probe," Nature Photonics 10, 580 (2016).
42. F. LaRocca, D. Nankivil, B. Keller, S. Farsiu, and J. A. Izatt, "Ultra-compact swept-source optical coherence tomography handheld probe with motorized focus adjustment (Conference Presentation)," in SPIE BiOS, (International Society for Optics and Photonics, 2017), 1005304-1005304-1005301.
43. J. Tokayer, Y. Jia, A.-H. Dhalla, and D. Huang, "Blood flow velocity quantification using split-spectrum amplitude-decorrelation angiography with optical coherence tomography," Biomedical optics express 4, 1909-1924 (2013).
44. O. M. Carrasco-Zevallos, R. Qian, N. Gahm, J. Migacz, C. A. Toth, and J. A. Izatt, "Long working distance OCT with a compact 2f retinal scanning configuration for pediatric imaging," Optics letters 41, 4891-4894 (2016).
45. A. V. Goncharov and C. Dainty, "Wide-field schematic eye models with gradient-index lens," JOSA A 24, 2157-2174 (2007).
46. A. W. Scott, S. Farsiu, L. B. Enyedi, D. K. Wallace, and C. A. Toth, "Imaging the infant retina with a hand-held spectral-domain optical coherence tomography device," American journal of ophthalmology 147, 364-373. e362 (2009).
47. C. D. Lu, M. F. Kraus, B. Potsaid, J. J. Liu, W. Choi, V. Jayaraman, A. E. Cable, J. Hornegger, J. S. Duker, and J. G. Fujimoto, "Handheld ultrahigh speed swept source optical coherence tomography instrument using a MEMS scanning mirror," Biomedical optics express 5, 293-311 (2014).
48. R. S. Maldonado, J. A. Izatt, N. Sarin, D. K. Wallace, S. Freedman, C. M. Cotten, and C. A. Toth, "Optimizing hand-held spectral domain optical coherence tomography imaging for neonates, infants, and children," Investigative ophthalmology & visual science 51, 2678-2685 (2010).
49. B. Braaf, K. V. Vienola, C. K. Sheehy, Q. Yang, K. A. Vermeer, P. Tiruveedhula, D. W. Arathorn, A. Roorda, and J. F. de Boer, "Real-time eye motion correction in phase-resolved OCT angiography with tracking SLO," Biomedical optics express 4, 51-65 (2013).
50. O. Carrasco-Zevallos, B. Keller, C. Viehland, L. Shen, G. Waterman, C. Chukwurah, P. Hahn, A. N. Kuo, C. A. Toth, and J. A. Izatt, "Real-time 4D Stereoscopic Visualization of Human Ophthalmic Surgery with Swept-Source Microscope Integrated Optical Coherence Tomography," Investigative Ophthalmology & Visual Science 56, 4085-4085 (2015).
51. C. Viehland, B. Keller, O. M. Carrasco-Zevallos, D. Nankivil, L. Shen, S. Mangalesh, D. T. Viet, A. N. Kuo, C. A. Toth, and J. A. Izatt, "Enhanced volumetric visualization for real time 4D intraoperative ophthalmic swept-source OCT," Biomedical Optics Express 7, 1815-1829 (2016).
52. O. Carrasco-Zevallos, B. Keller, C. Viehland, L. Shen, G. Waterman, B. Todorich, C. Shieh, P. Hahn, S. Farsiu, and A. Kuo, "Live volumetric (4D) visualization and guidance of in vivo human ophthalmic surgery with intraoperative optical coherence tomography," Scientific reports 6, 31689 (2016).
53. H. Foroosh, J. B. Zerubia, and M. Berthod, "Extension of phase correlation to subpixel registration," IEEE transactions on image processing 11, 188-200 (2002).
54. S. J. Chiu, X. T. Li, P. Nicholas, C. A. Toth, J. A. Izatt, and S. Farsiu, "Automatic segmentation of seven retinal layers in SDOCT images congruent with expert manual segmentation," Optics express 18, 19413-19428 (2010).
55. J. Campbell, M. Zhang, T. Hwang, S. Bailey, D. Wilson, Y. Jia, and D. Huang, "Detailed vascular anatomy of the human retina by projection-resolved optical coherence tomography angiography," Scientific reports 7, 42201 (2017).
56. A. Standard, "Z136. 1. American national standard for the safe use of lasers. American National Standards Institute," Inc., New York (1993).
57. D. Lepore, F. Molle, M. M. Pagliara, A. Baldascino, C. Angora, M. Sammartino, and G. E. Quinn, "Atlas of fluorescein angiographic findings in eyes undergoing laser for retinopathy of prematurity," Ophthalmology 118, 168-175 (2011).

What is claimed is:

1. An optical coherence tomography (OCT) imaging system comprising:
   optical elements configured to generate diverging light; and
   at least one mirror and a 5 focal length (5F) lens system including lenses that scan the diverging light onto a curved surface of an object for imaging of the object, wherein a field curvature of the 5F lens system as applied to the curved surface of the object substantially matches the curved surface of the object.

2. The OCT imaging system of claim 1, wherein the lens system comprises a relay telescope including the lenses that direct the diverging light onto the curved surface.

3. The OCT imaging system of claim 1, further comprising a lens system including the lenses that receive light that is scattered or reflected from the curved surface of the object.

4. The OCT imaging system of claim 1, further comprising an interferometer and detector, wherein the interferometer, detector and the lenses detect light reflected from the eye.

5. The OCT imaging system of claim 1, further comprising at least one electromechanical actuator configured to turn the at least one mirror for scanning the light, and
   wherein the at least one electromechanical actuator is at least one galvanometer.

6. The OCT imaging system of claim 1, wherein the at least one mirror comprises two mirrors, and
   wherein the OCT imaging system further comprises two galvanometers that are controlled to turn to angularly scan the light.

7. The OCT imaging system of claim 1, further comprising a collimating lens that is positioned to collimate the light, and
   wherein the collimating lens is positioned to receive the light and collimating the light upstream from scanning by the at least one mirror.

8. The OCT imaging system of claim 1, further comprising a short focal length, achromatic lens positioned to generate the diverging light.

9. The OCT imaging system of claim 1, wherein the object is an eye, and the curved surface is the surface of the retina of the eye.

10. The OCT imaging system of claim 1 further comprising a light source to generate the light, and
    wherein an optical fiber provides a pathway for the light between the light source and the at least one mirror.

11. A method for optical coherence tomography (OCT) imaging, the method comprising:
    using optical elements to generate diverging light; and
    using at least one mirror and a 5 focal length (5F) lens system including lenses that scan the diverging light onto a curved surface of an object for imaging of the object, wherein a field curvature of the 5F lens system as applied to the curved surface of the object substantially matches the curved surface of the object.

12. The method of claim 11, further comprising an interferometer and detector configured to detect light reflected from the eye.

13. The method of claim 12, further comprising an image processor configured to process a signal from the detector to generate an image of the eye.

14. The method of claim 11, further comprising at least one electromechanical actuator configured to turn the at least one mirror for scanning the light.

15. The method of claim 14, wherein the at least one electromechanical actuator is at least one galvanometer.

16. The method of claim 11, wherein the at least one mirror comprises two mirrors, and
    wherein the OCT imaging system further comprises two galvanometers configured to angularly scan the light.

17. The method of claim 11, wherein a scan range of the at least one mirror is in the range of about 28 degrees to about 100 degrees.

18. An optical coherence tomography (OCT) imaging probe comprising:
    an OCT system comprising:
      optical elements to generate diverging light; and
      at least one mirror and a 5 focal length (5F) lens system including lenses that scan the diverging light onto a curved surface of an object for imaging of the object, wherein a field curvature of the 5F lens system as applied to the curved surface of the object substantially matches the curved surface of the object; and
    a body defining a tip and an interior that contains the OCT system, wherein the tip defines an opening through which light from the OCT system passes.

19. The OCT imaging probe of claim 18, wherein the lens system comprises a relay telescope including the lenses that direct the diverging light onto the curved surface.

20. The OCT imaging probe of claim 18, further comprising a lens system including the lenses that receive light that is scattered or reflected from the curved surface of the object.

21. The OCT imaging probe of claim 18, further comprising an interferometer and detector, wherein the interferometer, detector and the lenses detect light reflected from the eye.

22. The OCT imaging probe of claim 18, wherein the at least one mirror comprises two mirrors, and
    wherein the OCT imaging system further comprises two galvanometers that are controlled to turn to angularly scan the light.

23. The OCT imaging probe of claim 18, further comprising a collimating lens configured to collimate the light, and
    wherein the collimating lens is positioned to receive the light and collimating the light upstream from scanning by the at least one mirror.

24. The OCT imaging probe of claim 18, further comprising a short focal length, achromatic lens positioned to generate the diverging light.

25. The OCT imaging probe of claim 18, wherein the object is an eye, and the curved surface is the surface of the retina of the eye.

26. The OCT imaging probe of claim 18, further comprising an optical fiber configured to be a pathway for light to the at least one mirror, and
    wherein the OCT imaging probe further comprises a light source to generate the light, and
    wherein the optical fiber provides a pathway for the light between the light source and the at least one mirror.

* * * * *